United States Patent
Ravalitera et al.

(10) Patent No.: US 8,985,536 B2
(45) Date of Patent: Mar. 24, 2015

(54) SUSPENDING ARM FOR AN ELECTRICAL APPLIANCE, ELECTRICAL EQUIPMENT FOR AN OPERATING ROOM

(71) Applicant: Maquet SAS, Ardon (FR)

(72) Inventors: Pierre Ravalitera, Neung sur Beuvron (FR); Adrien Monpou, Saran (FR)

(73) Assignee: Maquet SAS, Ardon (FR)

( * ) Notice: Subject to any disclaimer, the term of this patent is extended or adjusted under 35 U.S.C. 154(b) by 60 days.

(21) Appl. No.: 13/859,224

(22) Filed: Apr. 9, 2013

(65) Prior Publication Data

US 2013/0264448 A1 Oct. 10, 2013

(30) Foreign Application Priority Data

Apr. 10, 2012 (FR) ..................................... 12 53261

(51) Int. Cl.

| F16M 13/00 | (2006.01) |
| F16M 13/02 | (2006.01) |
| A61B 19/00 | (2006.01) |
| F16M 11/04 | (2006.01) |
| H01R 13/629 | (2006.01) |
| A61B 17/00 | (2006.01) |
| F21V 21/108 | (2006.01) |
| F21W 131/205 | (2006.01) |

(52) U.S. Cl.

CPC .............. *F16M 13/022* (2013.01); *A61B 19/26* (2013.01); *F16M 11/041* (2013.01); *A61B 2017/00477* (2013.01); *F16M 2200/065* (2013.01); *H01R 13/62922* (2013.01); *A61B 2019/265* (2013.01); *A61B 19/5202* (2013.01); *A61B 2017/00017* (2013.01); *F21V 21/108* (2013.01); *F21W 2131/205* (2013.01)

USPC ..................... 248/276.1; 248/279.1; 439/247; 33/503

(58) Field of Classification Search

CPC ........... A61B 19/2203; A61B 19/5202; A61B 2017/00477; A61B 2017/00017; A61B 2019/265; F16M 11/041; F21V 21/00; H01R 13/62922

USPC ............ 248/276.1, 324, 343, 279.1; 439/247, 439/248; 33/503

See application file for complete search history.

(56) References Cited

U.S. PATENT DOCUMENTS

| 3,164,355 A * | 1/1965 | Seitz et al. ..................... 248/324 |
| 6,217,363 B1 * | 4/2001 | Takata .......................... 439/342 |
| 6,788,018 B1 * | 9/2004 | Blumenkranz .......... 318/568.11 |
| 7,614,157 B2 * | 11/2009 | Granger ......................... 33/503 |

(Continued)

FOREIGN PATENT DOCUMENTS

EP 0967692 A2 12/1999

*Primary Examiner* — Anita M King

(74) *Attorney, Agent, or Firm* — Ware, Fressola, Maguire & Barber LLP

(57) ABSTRACT

A suspending arm comprises a multifunction head provided with a main transversal slide able to receive the engagement of a secondary slide of an electrical appliance, and a main electrical plug coupled with a longitudinal slide arranged so as to move the plug longitudinally between a retracted position in which it is retracted and an advanced position in which it protrudes so that it can be engaged with a secondary electrical plug of the electrical appliance, and thus ensure the mechanical and electrical connection between the multifunction head and the electrical appliance. An equipment for an operating room comprises a suspending arm supporting an electrical appliance comprising a secondary slide and a secondary electrical plug.

8 Claims, 2 Drawing Sheets

(56) References Cited

U.S. PATENT DOCUMENTS

| | | | |
|---|---|---|---|
| 7,779,548 B2* | 8/2010 | Ferrari | 33/503 |
| 8,171,650 B2* | 5/2012 | York et al. | 33/503 |
| 8,585,420 B2* | 11/2013 | Burbank et al. | 439/247 |
| 8,683,709 B2* | 4/2014 | York | 33/503 |
| 8,844,151 B2* | 9/2014 | Ferrari et al. | 33/503 |
| 2007/0142970 A1 | 6/2007 | Burbank et al. | |
| 2010/0038508 A1* | 2/2010 | Stoelinga | 248/276.1 |
| 2013/0264449 A1* | 10/2013 | Senelier et al. | 248/276.1 |

* cited by examiner

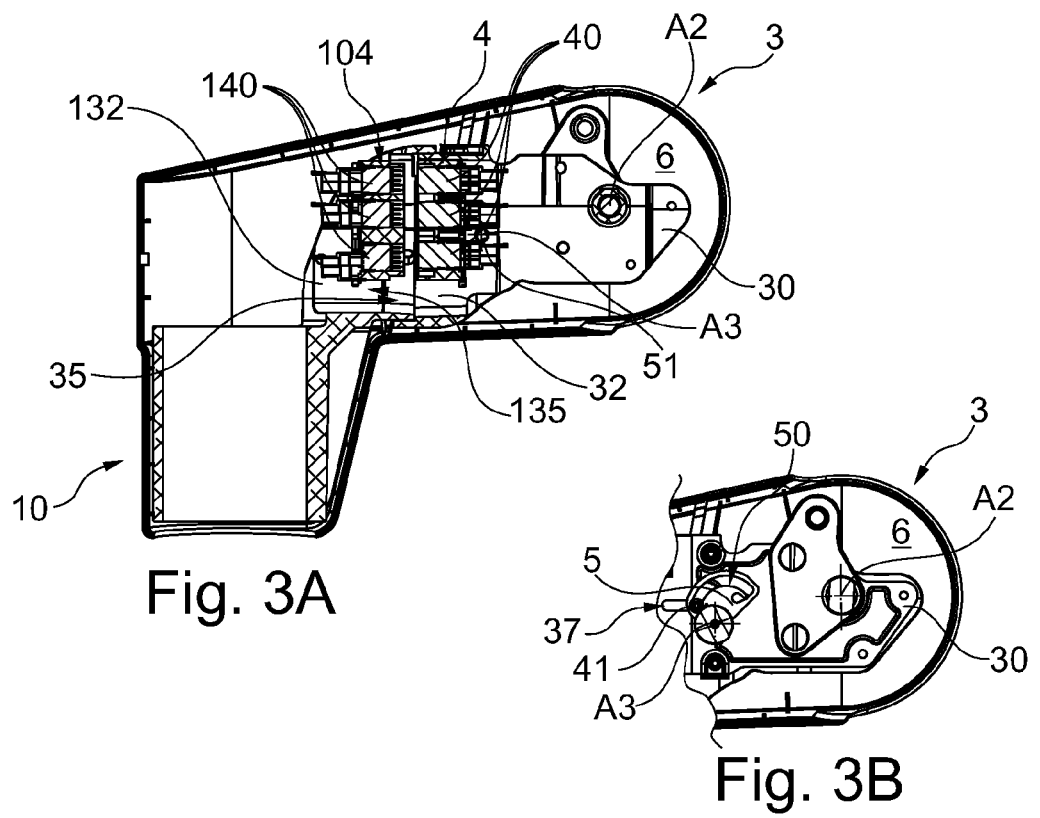
Fig. 3A
Fig. 3B
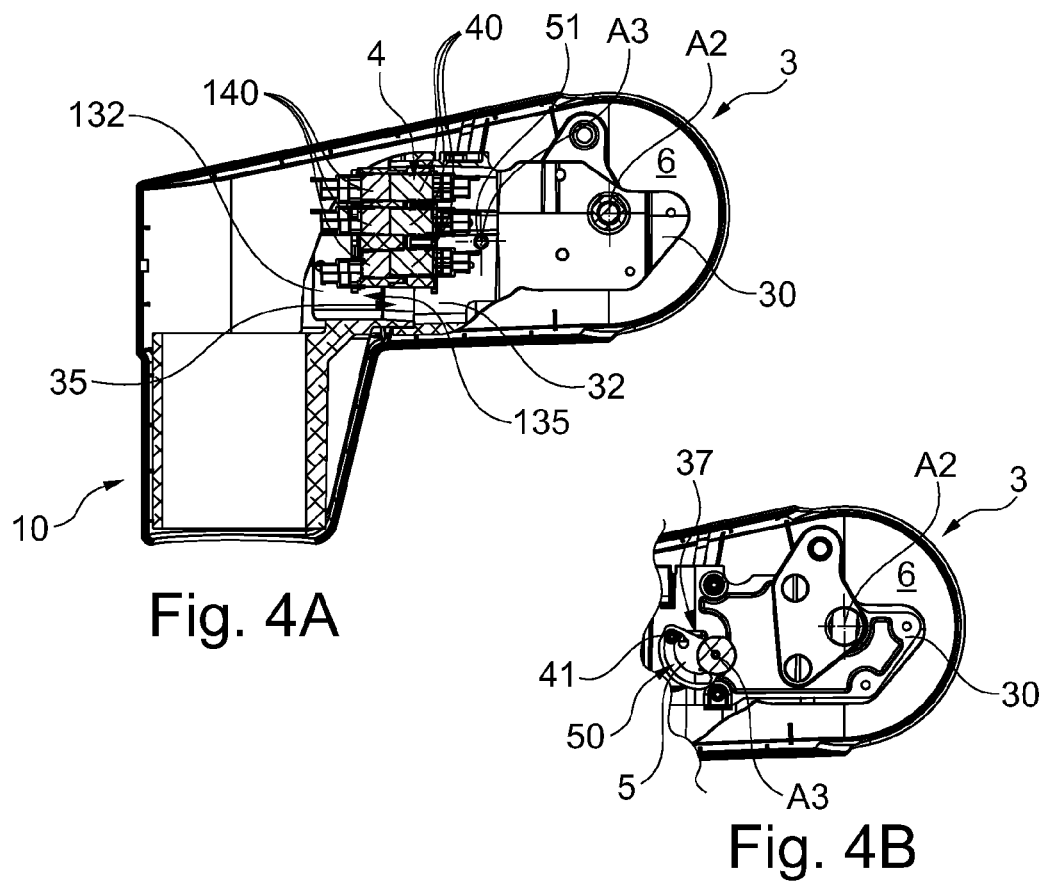
Fig. 4A
Fig. 4B

SUSPENDING ARM FOR AN ELECTRICAL APPLIANCE, ELECTRICAL EQUIPMENT FOR AN OPERATING ROOM

CROSS-REFERENCE TO RELATED APPLICATION

This application claims priority under 35 USC §119 to French Patent Application No. 12 53261 filed on Apr. 10, 2012, which application is hereby incorporated by reference in its entirety.

TECHNICAL FIELD

The invention relates to a suspending arm for an electrical appliance in particular for the equipment in an operating room, the suspending arm comprising a multifunction head provided with main mechanical and electrical connectors intended to cooperate respectively with secondary mechanical and electrical connectors of the electrical appliance in order to ensure removable mechanical and electrical connections between the electrical appliance and the multifunction head.

The invention also relates to an electrical equipment for an operating room comprising at least one suspending arm supporting an electrical appliance.

PRIOR ART

This type of suspending arm is used to suspend, for example from the ceiling of the operating room, an electrical appliance such as for example a lighting device, a monitor, a camera or any other appropriate apparatus. The arm is for example of the hinged type so as to be able to move and orient the electrical appliance in any appropriate position for the work of the medical staff. In general, operating rooms are provided with several arms supported by the same support. It is easily understood that it is very important that the mechanical and electrical connections between the electrical appliance and the suspending arm are reliable. It is sometimes necessary to remove one or several of these electrical appliances, for example for maintenance, or to install a specific electrical appliance. With this purpose, the operator must disassemble totally or partially the suspending arm in order to disconnect and disunite the electrical appliance from the suspending arm. This is a long and complex operation. Some electrical appliances require a particular electrical connection. In this case, the suspending arm must thus be modified in order to receive this particular electrical connection. This operation is work- and time-consuming so that the modularity of each suspending arm is limited.

Publication US 2007/142 970 describes a robot arm for a surgical operation, whose end is provided with a dismountable head. The arm and the head are provided with complementary grooves and ribs arranged transversally to the main axis of the arm and allowing their mutual engagement so that the head becomes mechanically connected to the arm.

Publication EP 0 967 692 describes an electrical connector comprising a plug in a case with respect to which said plug is mobile between a retracted position in which it is retracted inside the case and an advanced position in which it protrudes therefrom and allows an electrical connection.

However, these prior art devices do not optimally meet the user's needs.

DISCLOSURE OF THE INVENTION

The purpose of the invention is to find solutions for these drawbacks by proposing a suspending arm for an electrical appliance and an electrical equipment for an operating room, such solutions ensuring reliable mechanical and electrical connections, allowing a quick and reliable assembly-disassembly and connection-disconnection without any complicated disassembly of the suspending arm, and allowing the use of a plurality of electrical plugs so that the suspending arm is compatible with a large variety of electrical appliances.

For this purpose, the object of the invention is a suspending arm for an electrical appliance in particular for the equipment in an operating room, the suspending arm comprising a multifunction head provided with main mechanical and electrical connectors intended to cooperate respectively with secondary mechanical and electrical connectors of the electrical appliance in order to ensure removable mechanical and electrical connections between the electrical appliance and the multifunction head, wherein the main mechanical connector comprises a main fixed case arranged to define a main slide transversal to the longitudinal axis of the suspending arm and defining a main housing provided with a main frontal opening, in that the main electrical connector comprises at least one main electrical plug coupled with actuation means arranged so as to displace the plug longitudinally between a retracted position in which it is retracted inside the main housing and allows the engagement of the main and secondary mechanical connectors and an advanced position in which the plug protrudes at least partly through the main frontal opening so as to be engaged with the secondary electrical connector and to electrically connect the main and secondary electrical connectors to one another, in that the main electrical plug is prolonged by at least one guiding finger extending perpendicularly to the longitudinal axis, the guiding finger being arranged so as to extend through a longitudinal groove in the wall of the main case and to move in a cam groove in a cam able to swivel with respect to the main case so that the swiveling of the cam groove with respect to the main case causes the main electrical plug to move between its retracted and advanced positions.

The idea of the invention is to provide a mechanical connection by transversal engagement, coupled to an electrical connection by longitudinal engagement. This bidirectionality of the connections makes them more reliable. Thus, the fixation and the electrical connection are obtained by two distinct operations. The connectors ensuring each connection thus are dissociated from one another and are optimized so as to ensure at best each mechanical and electrical connection. Moreover, the electrical connection is carried out after the mechanical connection, therefore only when it is sure that the mechanical connection is reliable. There is thus a poor risk that, at the time of a connection, the electrical connectors are deteriorated by an unfortunate displacement between the electrical appliance and the suspending arm. Lastly, disassociating the electrical and mechanical connections allows, without being detrimental to the effectiveness of the mechanical connectors, to replace the electrical connectors in order to adapt them to specific electrical appliances.

The suspending arm according to the invention can advantageously present the following features:
  the main slide comprises a first pair of main slide portions opposite one another and a second pair of main slide portions oriented towards one another, the first and second pairs of main slide portions being shifted longitudinally and transversely from one another and separated from one another by the main housing;
  the cam is arranged so that it can be operated from the outside of the main case;
  the main electrical plug is arranged so that it can be disassociated from the main case, and the frontal opening is dimensioned so as to allow the complete extraction of the main electrical plug from the main housing;

the multifunction head is able to swivel with respect to a main axis at the end of the suspending arm and substantially perpendicular to the longitudinal axis;

the suspending arm comprises a casing provided with a frontal opening facing the main housing and arranged so as to jacket the main case.

The invention extends to an electrical equipment for an operating room comprising at least one suspending arm supporting an electrical appliance, wherein it comprises a suspending arm as described previously and at least one electrical appliance provided with a secondary mechanical connector forming a secondary slide able to cooperate with the main slide for ensuring the fixation of the electrical appliance to the multifunction head and at least one secondary electrical connector able to cooperate with the main electrical connector for ensuring the electrical connection of the electrical appliance to the arm.

The electrical appliance can comprise a secondary case defining a secondary housing for the secondary electrical plug and provided with a secondary frontal opening able to allow the passage of the main electrical plug between its retracted and advanced positions, the secondary slide comprising a first pair of secondary slide portions oriented towards one another and able to cooperate with the first pair of main slide portions, and a second pair of secondary slide portions opposite one another and able to cooperate with the second pair of main slide portions, the first and second pairs of secondary slide portions being shifted longitudinally and transversely from one another and separated from one another by the secondary housing.

BRIEF DESCRIPTION OF THE DRAWINGS

The present invention will be better understood and other advantages will emerge from the detailed description of an embodiment given as a nonrestrictive example and illustrated in the annexed drawings, in which:

FIGS. 3A and 3B are sectional views and a partial sectional view in two distinct planes of the suspending arm and the electrical appliance in FIGS. 2A at 2C after the mechanical interlocking and before the electrical connection between the main and secondary electrical connectors;

FIGS. 4A and 4B are views similar to those in FIGS. 3A and 3B after the mechanical interlocking and the electrical connection between the main and secondary electrical connectors.

DESCRIPTION OF THE EMBODIMENTS

The suspending arm according to the invention is intended for example to be used in an operating room for suspending electrical appliances used by the medical staff during surgical operations. These electrical appliances are for example monitors, lighting equipments, cameras or any other appropriate electrical appliance. In the Figures, the electrical appliance is only partly schematized. This appliance can be connected directly to the arm or via an intermediate piece as illustrated. For sake of simplification, the term 'electrical appliance' will also be used for the intermediate piece.

Figure 1:
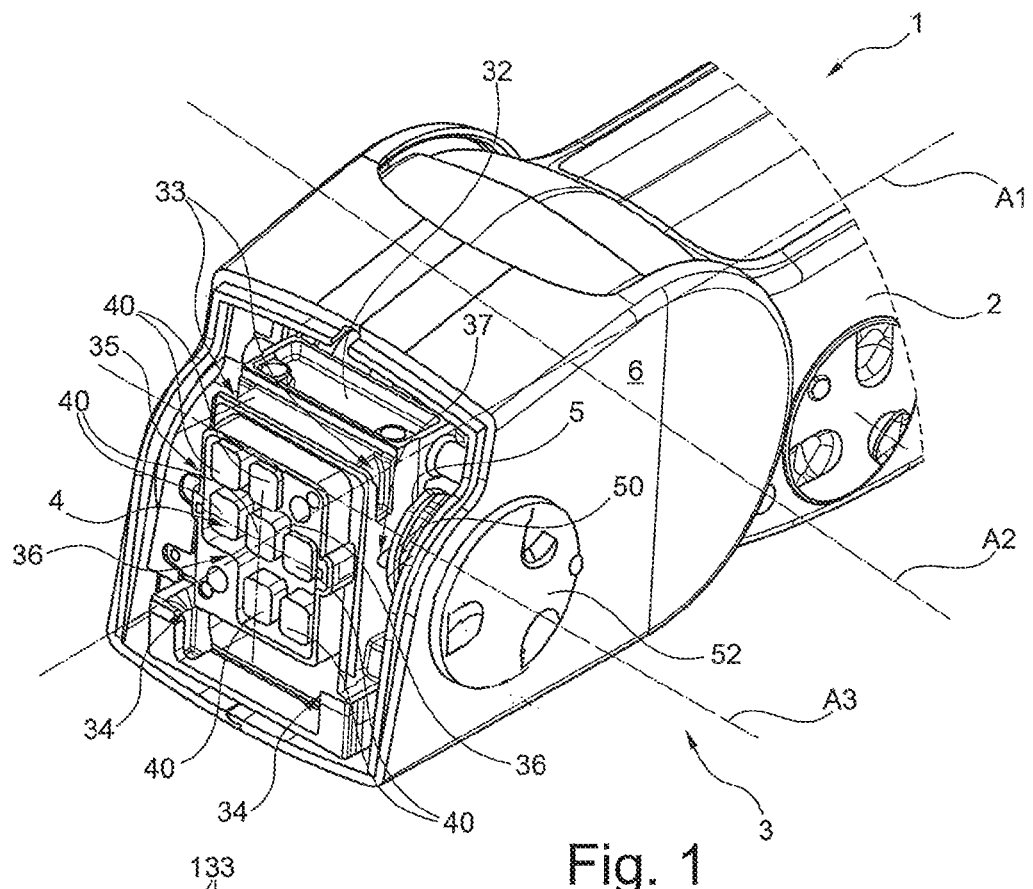
FIG. 1 is a perspective view of the end of a suspending arm according to the invention provided with a multifunction head and illustrating the main electrical and mechanical connectors of the multifunction head.

In reference to FIG. 1, the suspending arm 1 comprises a beam 2 having a longitudinal axis A1 and whose first end (not represented) is fixed in an hinged way with respect to a support (not represented). The second end of the beam 2 is provided with a multifunction head 3. Through this second end extends a main axis A2 substantially perpendicular to the longitudinal axis A1 and defining a main pivot connection allowing the swiveling of the multifunction head 3 with respect to the beam 2. This first pivot connection can be ensured by any known means. Thus, according to the means used, the slope of the multifunction head 3 can be fixed with respect to the beam 2, or variable so that the multifunction head 3 remains for example horizontal irrespective of the slope of the beam 2. This result can be obtained for example by applying the principle of the deformable parallelogram. In reference to FIGS. 2A to 4B, the multifunction head 3 comprises two clips 30 through which extend cylindrical bearings 31 partly forming the main pivot connection. These clips 30 are joined together by means of a main case 32 comprising main electrical plug 4.

Figures 2A, 2B, 2C:
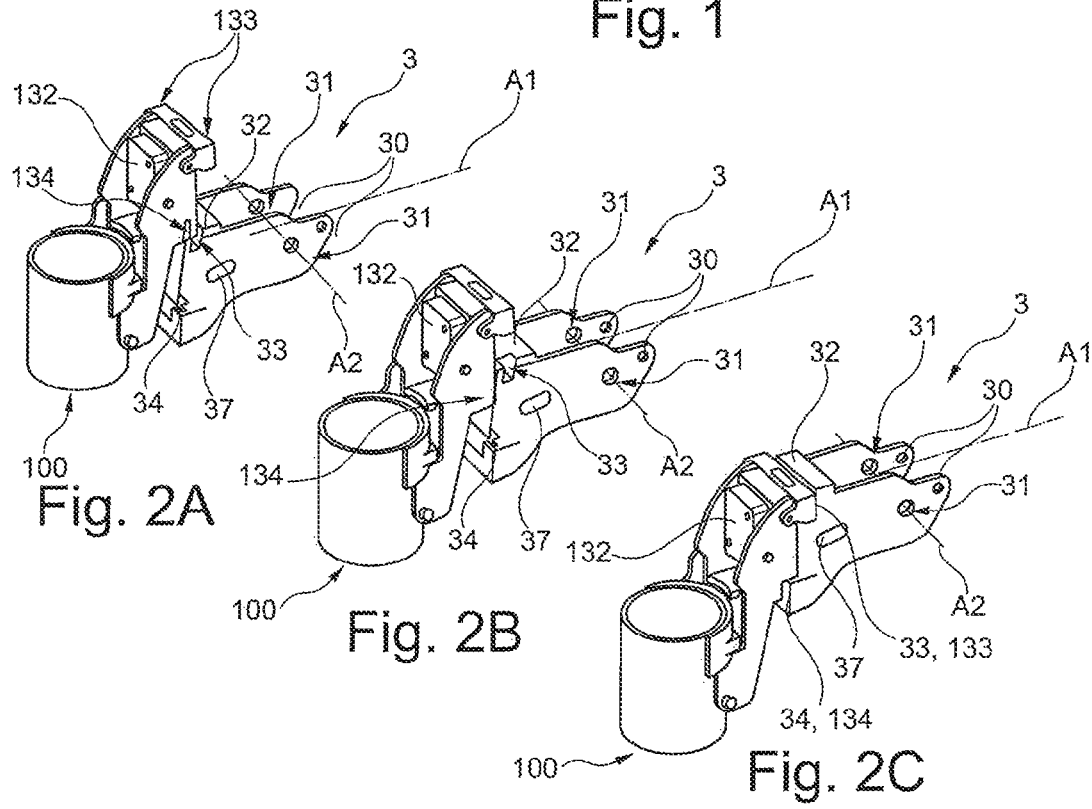
FIGS. 2A to 2C are perspective views of a part of the multifunction head and of an equipment illustrating the steps of mechanically interlocking an electrical appliance and the multifunction head of the suspending arm according to the invention with the co-operation between the main mechanical connector and the secondary mechanical connector.

In its upper part, the external edges of the main case 32 define a first pair of main slide portions 33 opposite one another. The first pair of main slide portions 33 is able to receive (as illustrated in FIGS. 2A to 2C detailed further below) the engagement of a first pair of secondary slide portions 133 oriented towards one another and supported by the electrical appliance 100. In its lower part, the main case 32 has the shape of a U whose branches define a second pair of main slide portions 34 oriented towards one another. The second pair of main slide portions 34 is able to receive (as illustrated in FIGS. 2A to 2C detailed further below) the engagement of a second pair of secondary slide portions 134 opposite one another and supported by the electrical appliance. The first and second pairs of main slide portions 33, 34 are arranged on both sides of the main housing 35 described further below. The U-shape is shifted longitudinally so that the second pair of main slide portions 34 protrudes with respect to the first pair of main slide portions 33 from the beam 3. The first and second pairs of main slide portions 33, 34 are transversely open upwards so that they allow the engagement of the first and second pairs of secondary slide portions 133, 134. The first and second pairs of main slide portions 33, 34 thus define a main mechanical connector able to interlock the multifunction head 3 and an electrical appliance 100 provided with a secondary mechanical connector.

In addition, the main case 32 defines a main housing 35 able to receive a main electrical plug 4 and provided with a main frontal opening opposite the main electrical plug 4. In the illustrated example, the main electrical plug 4 is of "multiple" type and comprises seven main electrical terminals 40. The main electrical plug 4 can of course comprise main electrical terminals in various number and/or arrangements. It is mounted so as to slide in the main case 32, while being guided by a longitudinal slide defined by the arrangement of the main electrical terminals 40 forming two re-entrant angles and the salient edges 36 formed in the main case 32 and emerging from the frontal opening. Via this longitudinal slide, the main electrical plug 4 is thus mobile between a retracted position (illustrated in FIGS. 1 and 3A) in which it is retracted, for example located flush with the main frontal opening or set back therefrom, and an advanced position in which it protrudes through the main frontal opening. Thus, in its retracted position, the main electrical plug 4 does not interfere with the trajectory of the first and second pairs of secondary slide portions 133, 134 during the engagement thereof in the first and second main slide portions 33, 34. Moreover, in its advanced position, the main electrical plug 4 protrudes through the main frontal opening so that it can engage in the electrical appliance 100 in order to electrically connect the main electrical plug 4 to a secondary electrical plug 104 of the secondary electrical connector of the electrical appliance 100. The main electrical plug 4 is of course electrically connected for example to a cable (not represented) in the beam 3. The cable is for example a power supply cable and/or a cable for transmitting signals, for example "high frequency" signals such as video HD signals, data-processing signals. The main electrical plug 4 thus forms the main electrical connector of the suspending arm 1.

The main case 32 is surrounded by a casing 6, opened opposite the main frontal opening. This casing 6 protects in particular the guiding fingers 41 described hereafter and the zones guiding them.

The main electrical plug 4 is provided with two guiding fingers 41 (only one of which is represented in FIGS. 1, 3B and 4B) extending laterally, perpendicularly to the longitudinal axis A1. These guiding fingers 41 extend through rectilinear longitudinal grooves 37 in the side walls of the main case 32 in which they can freely move in the longitudinal direction. Moreover, the guiding fingers 41 are guided in cam grooves 50 in cams 5 mounted so as to swivel with respect to a secondary axis A3 of the main case 32. The cam grooves 50 are curved and present a progressive radius with respect to the secondary axis A3. Thus, when a cam 5 swivels about its secondary axis A3, its cam groove 50 swivels and causes the corresponding guiding finger 41, guided in the longitudinal groove 37, to move in the longitudinal direction, which causes the main electrical plug 4 to move between its retracted and advanced positions. The two cams 5 can be connected by means of a control pin 51 coupled to a serrated actuation roller 52 accessible from the outside of the multifunction head (represented in FIG. 1). This serrated actuation roller 52 can be coupled with a lever (not represented) facilitating its actuation. According to an embodiment not represented, the suspending arm according to the invention comprises only one guiding finger, only one cam and only one longitudinal groove. According to another embodiment not represented, the suspending arm comprises only one cam but two fingers moving in the two longitudinal grooves.

The electrical appliance 100 comprises a secondary case 132 the upper part of which has the shape of a U whose branches define a first pair of secondary slide portions 133 oriented towards one another and able to receive the transversal engagement of the first pair of main slide portions 33. Moreover, the lower part defines a second pair of secondary slide portions 134 opposite one another and able to receive the transversal engagement of the second pair of main slide portions 34. The first and second pairs of secondary slide portions 133, 134 are distributed on both sides of the secondary housing 135 described further below. The U-shape is shifted longitudinally so that the first pair of secondary slide portions 133 protrudes with respect to the second pair of secondary slide portions 134 from the electrical appliance 100. The first and second pairs of secondary slide portions 133, 134 are transversely open downwards so that they allow the engagement of the first and second pairs of main slide portions 33, 34. They thus define a secondary mechanical connector able to interlock the electrical appliance 100 and the multifunction head 3.

In addition, the secondary case 132 defines a secondary housing 135 housing a secondary electrical plug 104 and provided with a secondary frontal opening opposite the secondary electrical plug 104. The secondary electrical plug 104 is fixed with respect to the secondary housing 135. In the illustrated example, the secondary electrical plug 104 is of "multiple" type and comprises seven secondary electrical terminals 140 able to cooperate with the seven main electrical terminals 40 of the multifunction head 3. The secondary electrical plug 104 can of course comprise a different number of secondary electrical terminals. The secondary electrical plug 104 is provided flush with the secondary frontal opening or set back therefrom so as not to interfere during the engagement of the first and second pairs of main 33, 34 and secondary 133, 134 slide portions. The secondary electrical plug 104 is of course electrically connected to the active part of the electrical appliance 100 (not represented). The secondary electrical plug 104 forms thus the secondary electrical connector of the suspending arm 1.

For mechanically interlocking the electrical appliance 100 and the suspending arm 1, as illustrated in FIG. 2A, the electrical appliance 100 is placed so that the first and second pairs of main slide portions 33, 34 and the first and second pairs of secondary slide portions 133, 134 are transversely respectively in alignment with one another, the main and secondary frontal openings being oriented towards one another while being vertically shifted from one another. Thus, the main and secondary frontal openings are substantially aligned in the same plane, for example perpendicular to the longitudinal axis A1. According to the illustrated example, the electrical appliance 100 is thus arranged above the multifunction head 3.

As illustrated in FIG. 2B, the electrical appliance 100 is then moved with respect to the multifunction head 3 in the transversal direction T, the first and second pairs of main slide portions 33, 34 and the first and second pairs of secondary slide portions 133, 134 being always in alignment with one another. Thus, the main and secondary mechanical connectors engage in one another, the main and secondary frontal openings passing very close to one another so that the main 4 and secondary 104 electrical plugs pass in front of one another.

As illustrated in FIGS. 2C, 3A and 3B, the mechanical connection is ensured when the bottoms of the first and second pairs of main 33, 34 and secondary 133, 134 slide portions are against one another. In this step, the main and secondary frontal openings are opposite one another, the main electrical terminals 40 being opposite the secondary electrical terminals 140 but at a distance therefrom. The main electrical plug 4 is still in its retracted position, the guiding finger 41 being located at the end of the cam groove 50 having the shortest radius.

As illustrated in FIGS. 4A and 4B, for ensuring the electrical connection, the serrated actuation roller 52 is operated so as to rotate, in this example counterclockwise. This operation causes the cam 5 to rotate, which comprises the cam groove 50 moving the guiding finger 41 in the transversal groove 37 until the guiding finger 41 reaches the end of the cam groove 50 having the largest radius. The main electrical plug 4 is thus moved from its retracted position to its advanced position in which it is inserted into the secondary housing 135 so that the main terminals 40 and the secondary terminals 140 come into contact with one another.

The electrical appliance 100 can be disassembled at any time. To this end, the main electrical plug 4 is disengaged from the secondary electrical plug 104 by actuating the serrated actuation roller 52 clockwise so as to move the main electrical plug 4 from its advanced position to its retracted position. Then, the electrical appliance 100 is freed transversely by making the first main 33, 34 and secondary 133, 134 slide portions slide relative to one another. Once the electrical appliance 100 is disassembled, it can be replaced with any other equivalent electrical appliance.

The invention makes it possible to achieve the objectives previously mentioned. Indeed, the suspending arm 1 according to the invention thus makes it possible to obtain in a simple and reliable manner an effective mechanical connection thanks to a simple vertical locking. Once the mechanical connection is ensured, the electrical connection can be carried out in a simple and fast way by rotating the serrated actuation roller 52.

Of course the present invention is not limited to the preceding description of one of its embodiments, which can be somewhat modified while remaining within the scope of the invention. Thus, for example, according to an alternative embodiment not represented, the cam can be actuated by means of a mechanical, pneumatic actuator or of any other appropriate actuator. Moreover, the translation of the main electrical plug is obtained with the help of equivalent mechanical means such as for example a camshaft system.

What is claimed is:

1. A suspending arm for an electrical appliance in particular for the equipment in an operating room, said suspending arm comprising a multifunction head provided with main mechanical and electrical connectors intended to cooperate respectively with secondary mechanical and electrical connectors of said electrical appliance in order to ensure removable mechanical and electrical connections between said electrical appliance and said multifunction head, wherein said main mechanical connector comprises a main fixed case arranged so as to define a main slide transversal to the longitudinal axis of said suspending arm and defining a main housing provided with a main frontal opening, wherein said main electrical connector comprises at least one main electrical plug coupled with actuation means arranged so as to move said plug longitudinally between a retracted position in which it is retracted into said main housing and allows the engagement of said main and secondary mechanical connectors and an advanced position in which it protrudes at least partly through said main frontal opening so as to be engaged with said secondary electrical connector and to electrically connect said main and secondary electrical connectors to one another, wherein said main electrical plug is prolonged by at least one guiding finger extending perpendicularly to said longitudinal axis, said guiding finger being arranged so as to extend through a longitudinal groove in the wall of said main case and to move in a cam groove in a cam able to swivel with respect to said main case so that the swiveling of said cam groove with respect to said main case causes said main electrical plug to move between its retracted and advanced positions.

2. The suspending arm according to claim 1, wherein said main slide comprises a first pair of slide main portions opposite one another and a second pair of slide main portions oriented towards one another, said first and second pairs of slide main portions being shifted longitudinally and transversely from one another and separated from one another by said main housing.

3. The suspending arm according to claim 1, wherein said cam is arranged so that it can be operated from the outside of said main case.

4. The suspending arm according to claim 1, wherein said main electrical plug is arranged so that it can be disassociated from said main case and wherein said frontal opening is dimensioned so as to allow the complete extraction of said main electrical plug from said main housing.

5. The suspending arm according to claim 1, wherein said multifunction head is able to swivel with respect to a main axis at the end of said suspending arm and substantially perpendicular to said longitudinal axis.

6. The suspending arm according to claim 1, wherein it comprises a casing provided with a frontal opening facing said main housing and arranged to jacket said main case.

7. An electrical equipment for an operating room comprising at least one suspending arm supporting an electrical appliance, wherein it comprises a suspending arm according to claim 1 and at least one electrical appliance provided with a secondary mechanical connector forming a secondary slide able to cooperate with said main slide for ensuring the fixation of said electrical appliance to the multifunction head and at least one secondary electrical connector able to cooperate with said main electrical connector for ensuring the electrical connection of said electrical appliance to said arm.

8. The electrical component according to claim 7, wherein said electrical appliance comprises a secondary case defining a secondary housing for said secondary electrical plug and provided with a secondary frontal opening able to allow the passage of said main electrical plug between its retracted and advanced positions, wherein said secondary slide comprises a first pair of secondary slide portions oriented towards one another and able to cooperate with said first pair of main slide portions, and a second pair of secondary slide portions opposite one another and able to cooperate with said second pair of main slide portions, said first and second pairs of secondary slide portions being shifted longitudinally and transversely from one another and separated from one another by said secondary housing.

* * * * *